United States Patent
Liu et al.

(10) Patent No.: US 12,029,839 B2
(45) Date of Patent: *Jul. 9, 2024

(54) MEMBRANE OXYGENATORS

(71) Applicant: JIANGSU STMED TECHNOLOGY CO., LTD., Jiangsu (CN)

(72) Inventors: Ridong Liu, Suzhou (CN); Peng Liu, Suzhou (CN); Yujie Liu, Suzhou (CN)

(73) Assignee: JIANGSU STMED TECHNOLOGY CO., LTD., Suzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/531,750

(22) Filed: Dec. 7, 2023

(65) Prior Publication Data
US 2024/0100233 A1 Mar. 28, 2024

Related U.S. Application Data

(63) Continuation-in-part of application No. PCT/CN2021/124833, filed on Oct. 20, 2021.

(30) Foreign Application Priority Data

Jul. 14, 2021 (CN) .......................... 202110794390.4

(51) Int. Cl.
*A61M 1/16* (2006.01)
*A61M 1/36* (2006.01)

(52) U.S. Cl.
CPC ........ *A61M 1/1698* (2013.01); *A61M 1/1623* (2014.02); *A61M 1/1629* (2014.02); *A61M 1/3623* (2022.05)

(58) Field of Classification Search
CPC .............. A61M 1/1698; A61M 1/1623; A61M 1/1629; A61M 1/3623
See application file for complete search history.

(56) References Cited

U.S. PATENT DOCUMENTS 4,620,965 A 11/1986 Fukusawa et al.
8,388,566 B2 * 3/2013 Reggiani ............ A61M 1/3627
604/4.01

(Continued)

FOREIGN PATENT DOCUMENTS

CN 1042082 A 5/1990
CN 102753210 A 10/2012

(Continued)

OTHER PUBLICATIONS

The Third Office Action in Chinese Application No. 202110794390.4 mailed on Jun. 15, 2022, 10 pages.

(Continued)

*Primary Examiner* — Philip R Wiest
(74) *Attorney, Agent, or Firm* — METIS IP LLC

(57) ABSTRACT

Embodiments of the present disclosure provide a membrane oxygenator including an upper cover, a lower cover, a shell, and an oxygenation structure. Both ends of the shell are connected with the upper cover and the lower cover respectively. The oxygenation structure includes a mandrel, an oxygen pressure membrane, and a temperature-changing membrane, wherein an upper end of the mandrel enters a first blood path space of the upper cover, a lower end of the mandrel is opposite to a blood outlet of the lower cover, the oxygen pressure membrane is provided around the mandrel and connects a first gas path space and a second gas path space, and the temperature-changing membrane wraps around the oxygen pressure membrane. A gap is provided between the temperature-changing membrane and an inner wall of the shell. A blood inlet is provided on the shell near the upper cover.

10 Claims, 7 Drawing Sheets

(56) References Cited

U.S. PATENT DOCUMENTS

| | | | |
|---|---|---|---|
| 11,724,014 B2* | 8/2023 | Liu | A61M 1/3627 |
| | | | 422/48 |
| 11,730,870 B2* | 8/2023 | Liu | A61M 1/3666 |
| | | | 604/6.13 |
| 2012/0193289 A1* | 8/2012 | Cloutier | A61M 1/1698 |
| | | | 422/46 |
| 2013/0101465 A1 | 4/2013 | Galavotti | |
| 2013/0209314 A1* | 8/2013 | Roller | A61M 1/36 |
| | | | 422/46 |
| 2014/0030149 A1* | 1/2014 | Takeuchi | A61M 1/3623 |
| | | | 422/48 |
| 2016/0296685 A1* | 10/2016 | Wu | A61M 60/113 |
| 2019/0030461 A1 | 1/2019 | Dyer | |
| 2020/0206404 A1* | 7/2020 | Wu | A61M 1/1629 |
| 2020/0345717 A1* | 11/2020 | Wang | C07D 471/04 |

FOREIGN PATENT DOCUMENTS

| | | |
|---|---|---|
| CN | 103209722 A | 7/2013 |
| CN | 103547298 A | 1/2014 |
| CN | 109224163 A | 1/2019 |
| CN | 113509605 A | 10/2021 |
| WO | 2009098457 A2 | 8/2009 |

OTHER PUBLICATIONS

Decision to Grant a Patent in Chinese Application No. 202110794390.4 mailed on Aug. 23, 2022, 6 pages.
International Search Report in PCT/CN2021/124833 mailed on Mar. 29, 2022, 7 pages.
Written Opinion in PCT/CN2021/124833 mailed on Mar. 29, 2022, 8 pages.

* cited by examiner

MEMBRANE OXYGENATORS

CROSS-REFERENCE TO RELATED APPLICATIONS

This application is a continuation-in-part application of International Application No. PCT/CN2021/124833, filed on Oct. 20, 2021, which claims priority to Chinese Patent Application No. 202110794390.4, filed on Jul. 14, 2021, the entire contents of each of which are hereby incorporated by reference.

TECHNICAL FIELD

The present disclosure relates to the field of medical devices, particularly to membrane oxygenators.

BACKGROUND

A membrane oxygenator is a medical device that serves as a substitute for lung functions during cardiac arrest. The membrane oxygenator has the function of regulating the contents of oxygen and carbon dioxide in the blood, which is an essential medical device for a cardiovascular surgery, as well as the treatment of acute respiratory diseases and the waiting stage of lung transplantation. Based on the principle of air exchange in alveoli, a membrane oxygenator integrates functions of oxygenation, temperature adjustment, blood storage, and filtration. The working principle of the membrane oxygenator is as follows: venous blood in the body is led out of the body and passed through the membrane oxygenator for oxygen and carbon dioxide exchange to become arterial blood, which is then returned to the arterial system of the body to maintain oxygenated blood supply to the organs and tissues. The membrane oxygenator temporarily replaces lung functions during a surgery to meet a patient's needs during the operation.

Air exchange capacity is a major functional indicator of the membrane oxygenator. The air exchange capacity is usually positively correlated with an area of an oxygen pressure membrane. However, blood preloading and the contact area between blood and artificial materials also increase while increasing the area of the oxygen pressure membrane, leading to more blood loss and destruction, which may have a negative impact on the patient's postoperative recovery.

Therefore, it is desirable to provide a membrane oxygenator with improved air exchange capacity.

SUMMARY

One or more embodiments of the present disclosure provide a membrane oxygenator. The membrane oxygenator may include an upper cover, a lower cover, a shell, an oxygenation structure, a gap, and a spoiler structure. The upper cover may be sequentially divided into a first blood path space, a first gas path space, and a first water path space from a center to an outer edge, and the upper cover may be provided with an air inlet connected with the first gas path space, a first vent connected with the first blood path space, and a water inlet connected with the first water path space. The lower cover may be sequentially divided into a second blood path space, a second gas path space, and a second water path space from the center to the outer edge, and the lower cover may be provided with a blood outlet connected with the second blood path space, an air outlet connected with the second gas path space, and a water outlet connected with the second water path space. Both ends of the shell may be connected with the upper cover and the lower cover respectively, and a blood inlet connected with an inner cavity of the shell may be provided on the shell near the upper cover. The oxygenation structure may be provided in the inner cavity of the shell. The oxygenation structure may include a mandrel, an oxygen pressure membrane, and a temperature-changing membrane. An upper end of the mandrel may enter the first blood path space. The upper end of the mandrel may be opposite to the first vent. A lower end of the mandrel may be opposite to the blood outlet. The oxygen pressure membrane may be provided around the mandrel. The oxygen pressure membrane may connect the first gas path space and the second gas path space. The temperature-changing membrane may wrap around the oxygen pressure membrane. The temperature-changing membrane may be connected with the first water path space and the second water path space. A gap may be provided between the temperature-changing membrane and an inner wall of the shell. A width of the gap may gradually decrease from the upper cover to the lower cover. The oxygenator may further include a spoiler structure for directing a lateral flow of blood. The spoiler structure may be provided between the shell and the temperature-changing membrane. The spoiler structure may include a plurality of protrusions protruding from the inner wall of the shell towards the temperature-changing membrane, and the protrusions may be provided on the inner wall of the shell.

In some embodiments, the membrane oxygenator may further include a first plugging layer, the first plugging layer may be provided at a junction of the shell and the upper cover; and a second plugging layer may be provided at a junction of the shell and the lower cover.

In some embodiments, the oxygen pressure membrane may include a plurality of ventilation pipes, which may be hollow pipes with openings at both ends. One end of each ventilation pipe may be penetrated into the first plugging layer and connected with the first gas path space, and the other end of each ventilation pipe may be penetrated into the second plugging layer and connected with the second gas path space.

In some embodiments, the temperature-changing membrane may include a plurality of variable temperature tubes, which may be hollow pipes with openings at both ends. One end of each variable temperature tube may be penetrated into the first plugging layer and connected with the first water path space, and the other end of each variable temperature tube may be penetrated into the second plugging layer and connected with the second water path space.

In some embodiments, the plurality of protrusions may be distributed in a stepped manner. A distance between protrusions close to the upper cover and the temperature-changing membrane may be greater than a distance between protrusions close to the lower cover and the temperature-changing membrane.

In some embodiments, the upper cover may be further provided with a recirculation port. The recirculation port may be connected with the first vent.

In some embodiments, the shell may be provided with a second vent.

In some embodiments, the second vent may be provided with a one-way permeable membrane. The one-way permeable membrane may be used to retain liquid in the shell and to allow air bubbles in the liquid to discharge the shell.

In some embodiments, the shell may be a cylindrical shell. An inner diameter of the shell may decrease sequentially from the upper cover to the lower cover; and a cross-section of the mandrel may decrease gradually from the upper cover to the lower cover.

In some embodiments, the upper cover may include a first partition ring and a second partition ring. The second partition ring may be provided around the first partition ring. The first partition ring may separate the first blood path space from the first gas path space, and the second partition ring separates the first gas path space from the first water path space. The lower cover may include a third partition ring and a fourth partition ring. The fourth partition ring may be provided around the third partition ring. The third partition ring may separate the second blood path space from the second gas path space, and the fourth partition ring may separate the second gas path space from the second water path space.

BRIEF DESCRIPTION OF THE DRAWINGS

The present disclosure will be further illustrated by way of exemplary embodiments. These exemplary embodiments will be described in detail by way of drawings. These embodiments are non-limiting exemplary embodiments, in which like reference numerals represent similar structures, wherein.

DETAILED DESCRIPTION

Figure 1:
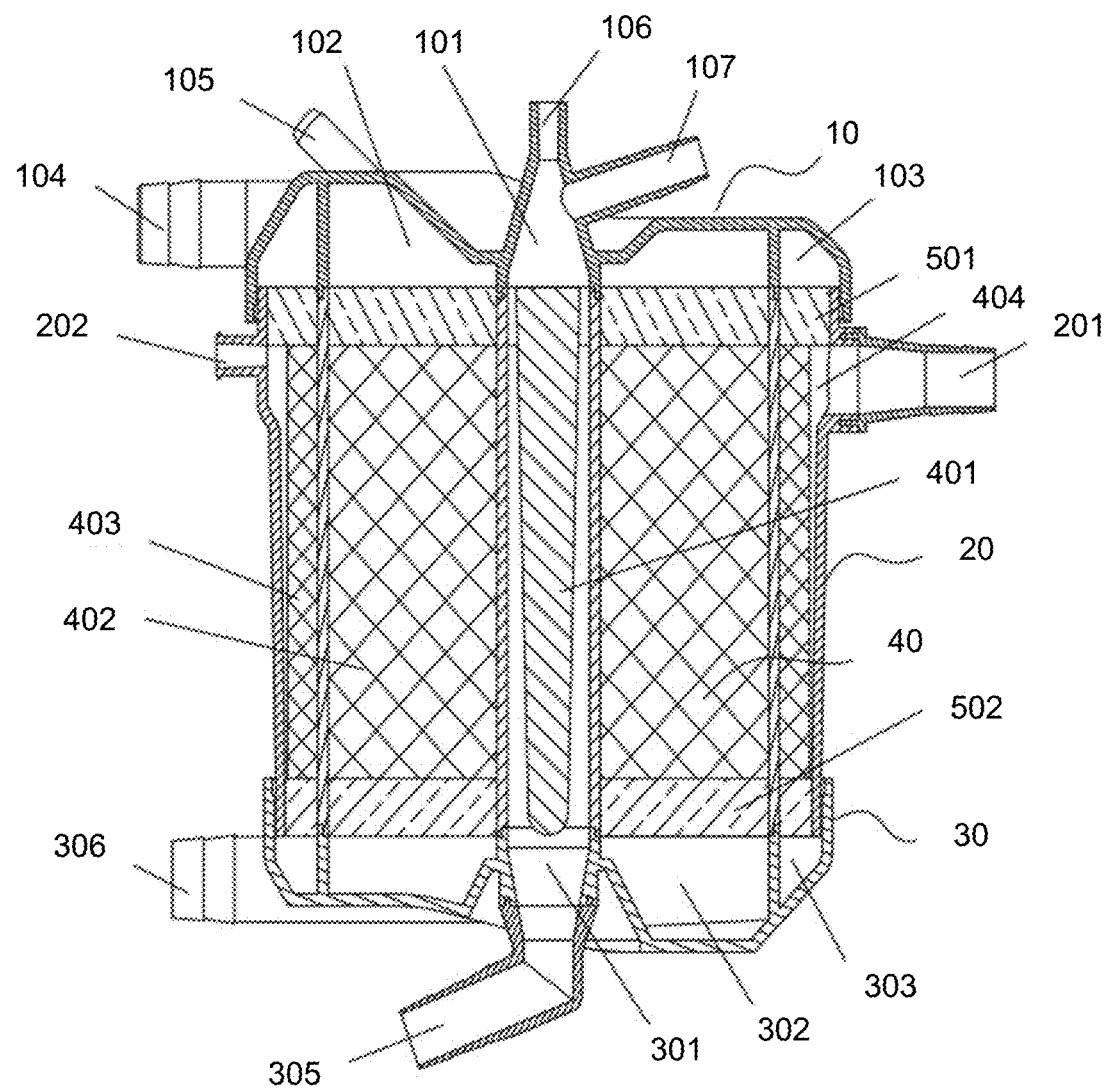
FIG. 1 is a schematic structural diagram illustrating a membrane oxygenator according to some embodiments of the present disclosure.

In order to more clearly illustrate technical solutions of the embodiments of the present disclosure, a brief introduction of the drawings referred to the description of the embodiments is provided below. Obviously, the accompanying drawings in the following description are only some examples or embodiments of the present specification, and it is possible for those having ordinary skills in the art to apply the present disclosure to other similar scenarios on the basis of these drawings without creative labor. Unless apparent from the linguistic context or otherwise indicated, the same symbols in the drawings represent the same structure or operation.

As shown in this specification and the claims, unless the context explicitly indicates otherwise, words such as "one," "a," "an," and/or "the" are not limited to singular forms and may also include plural forms. In general, the terms "comprising" and "including" only indicate the inclusion of specifically identified steps and elements, and these steps and elements do not constitute an exclusive listing. Methods or devices may also include other steps or elements.

A membrane oxygenator is a medical device capable of performing extracorporeal air exchange to replace lung functions in a surgery or a life-sustaining procedure.

FIG. 1 is a schematic structural diagram illustrating a membrane oxygenator according to some embodiments of the present disclosure.

In some exemplary embodiments, as shown in FIG. 1, the membrane oxygenator may include an upper cover 10, a lower cover 30, a shell 20, and an oxygenation structure 40. The upper cover 10 refers to an upper end structure of the oxygenator, and the lower cover 30 refers to a lower end structure of the oxygenator. The shell 20 may be configured to carry main components of the oxygenator. In some embodiments, both ends of the shell 20 may be connected with the upper cover 10 and the lower cover 30 respectively. The oxygenation structure 40 may be provided inside the shell 20 and used for exchange of oxygen and carbon dioxide to convert venous blood into arterial blood. A connection between the shell 20 and the upper cover 10 or the lower cover 30 may include, but is not limited to, a socket connection, a snap-fit connection, etc.

In some embodiments, the membrane oxygenator may also include a spoiler structure configured to direct a lateral flow of blood.

In some embodiments, the spoiler structure may be provided between the shell 20 and a temperature-changing membrane 403. In some embodiments, the spoiler structure may include a plurality of protrusions protruding from an inner wall of the shell 20 towards the temperature-changing membrane 403. The protrusions may be provided on the inner wall of the shell 20. More details regarding the spoiler structure may be found in FIG. 4 and related descriptions thereof.

In some embodiments, the upper cover 10 may be sequentially divided into a first blood path space 101, a first gas path space 102, and a first water path space 103 from a center to an outer edge. The first blood path space 101 may be a cavity for holding blood. The first gas path space 102 may be a cavity for holding air. The first water path space 103 may be a cavity for holding water flowing from a variable temperature water tank.

In some embodiments, the upper cover 10 may be provided with an air inlet 105 connected with the first gas path space 102, a first vent 106 connected with the first blood path space 101, and a water inlet 104 connected with the first water path space 103. The air inlet 105 may be used for an entry of oxygen from an oxygen source. The water inlet 104 may be used for an entry of water from the variable temperature water tank.

In some embodiments, the first vent 106 may be opposite to an upper end of a mandrel 401 and configured to discharge air bubbles from blood. In some embodiments, when air in the membrane oxygenator is gathered near the mandrel 401 along a blood flow direction, the air bubbles in the blood move upwards and are likely to be discharged through the first vent 106 at a top of the upper cover 10. More details regarding the mandrel 401 may be found in relevant descriptions below.

In some embodiments, the upper cover 10 may be made of a transparent material, so as to visually observe whether there are residual air bubbles inside the oxygenator, and determine whether there is a safety risk for the product (the oxygenator) or an overall circuit by observing the accumulation of air bubbles at the top during a surgery, thereby taking measures in time to avoid severe consequences.

In some embodiments, the upper cover 10 may be also provided with a recirculation port 107 connected with the first vent 106.

The recirculation port 107 serves as a channel for drawing out oxygenated blood. In some embodiments, when there is a need to draw out the oxygenated blood for another purpose, the oxygenated blood may be extracted from a vicinity of the mandrel 401 through connecting the upper cover 10 with the recirculation port 107. The connection between the upper cover 10 and the recirculation port 107 may be a socket connection, a threaded connection, etc.

In some embodiments, the upper cover 10 may also include an upper cover body, a first partition ring (not shown in the figure), and a second partition ring (not shown in the figure).

The upper cover body refers to a main structure of the upper cover 10. In some embodiments, the upper cover body may include an opening and a bottom opposite to the opening. The bottom may protrude in a direction away from the opening, making a middle of the upper cover body concave.

The first partition ring may be configured to separate the first blood path space 101 from the first gas path space 102. In some embodiments, the first partition ring may be provided inside the upper cover body and divide a concave space of the upper cover body into an inner space and an outer space. The inner space of the first partition ring may be the first blood path space 101.

The second partition ring may be configured to separate the first blood path space 101 from the first water path space 103. In some embodiments, the second partition ring may be provided around the first partition ring and divide a space outside the first partition ring into an inner space and an outer space. A space between the first partition ring and the second partition ring may be the first gas path space 102, and a space between the second partition ring and an edge of the upper cover body may be the first water path space 103.

In some embodiments, the air inlet 105 and water inlet 104 may be both provided on the upper cover body, the air inlet 105 may be located between the first partition ring and the second partition ring, and the water inlet 104 may be located between the second partition ring and the edge of the upper cover body.

In some embodiments, the lower cover 30 may sequentially divided into a second blood path space 301, a second gas path space 302, and a second water path space 303 from the center to the outer edge. Different from the first blood pathway space 101, the second blood pathway space 301 may be a cavity for holding oxygenated blood (i.e., arterial blood). The second air pathway space 302 may be a cavity for holding carbon dioxide gas. The second water pathway space 303 may be a space for holding water from the variable temperature tubes.

In some embodiments, the lower cover 30 may be provided with a blood outlet 305 connected with the second blood path space 301, an air outlet (not shown in the figure) connected with the second gas path space 302, and a water outlet 306 connected with the second water path space 303.

The blood outlet 305 may be used for outflowing of the oxygenated blood (i.e., the arterial blood). In some embodiments, the blood outlet 305 may be located at a center of a bottom of the membrane oxygenator, allowing a doctor to maximize the recovery of residual blood after surgery, reducing the risk of cross-infection caused by allogeneic blood transfusion, and reducing the use of stored blood.

The air outlet may be configured to remove carbon dioxide from the blood. In some embodiments, the water outlet 306 may be configured to return the water from the variable temperature tubes to the variable temperature water tank.

In some embodiments, the lower cover 30 may also include a lower cover body, a third partition ring (not shown in the figure), and a fourth partition ring (not shown in the figure).

The lower cover body refers to a main structure of the lower cover 30. In some embodiments, the lower cover body may include an opening and a bottom opposite to the opening. The bottom may protrude in a direction away from the opening, making a middle of the lower cover body concave.

The third partition ring may be configured to separate the second blood path space 301 from the second gas path space 302. In some embodiments, the third partition ring may be provided inside the lower cover body and divide a concave space of the lower cover body into an inner space and an outer space. The inner space of the third partition ring may be the second blood path space 301.

The fourth partition ring may be configured to separate the second gas path space 302 from the second water path space 303. In some embodiments, the fourth partition ring may be provided around the third partition ring and divide a space outside the third partition ring into an inner space and an outer space. A space between the third partition ring and the fourth partition ring may be the second gas path space 302, and a space between the fourth partition ring and an edge of the lower cover body may be the second water path space 303.

In some embodiments, the blood outlet 305, the air outlet, and the water outlet 306 may all be provided on the upper cover body. The blood outlet 305 may be located inside the third partition ring, the air outlet may be located between the third partition ring and the fourth partition ring, and the water outlet 306 may be located between the fourth partition ring and the edge of the upper cover body.

In some embodiments, both ends of the shell 20 may be connected with the upper cover 10 and the lower cover 30 respectively, and a blood inlet 201 connected with an inner cavity of the shell may be provided on the shell 20 near the upper cover 10.

In some embodiments, the shell 20 may be a hollow part with openings at both ends. For example, the shell 20 may be cylindrical. In some embodiments, a first shell partition part and a second shell partition part may be provided inside the shell 20. The first shell partition part and the second shell partition part may be annular parts, and both ends of the first shell partition part may be respectively connected with the first partition ring of the upper cover 10 and the third partition ring of the lower cover 30. Both ends of the second shell partition part may be respectively connected with the second partition ring of the upper cover 10 and the fourth partition ring of the lower cover 30. A connection between the first shell partition part and the first and third partition rings, and a connection between the second shell partition part and the second and fourth partition rings may be a welding connection, a snap-fit connection, etc.

Figure 2:
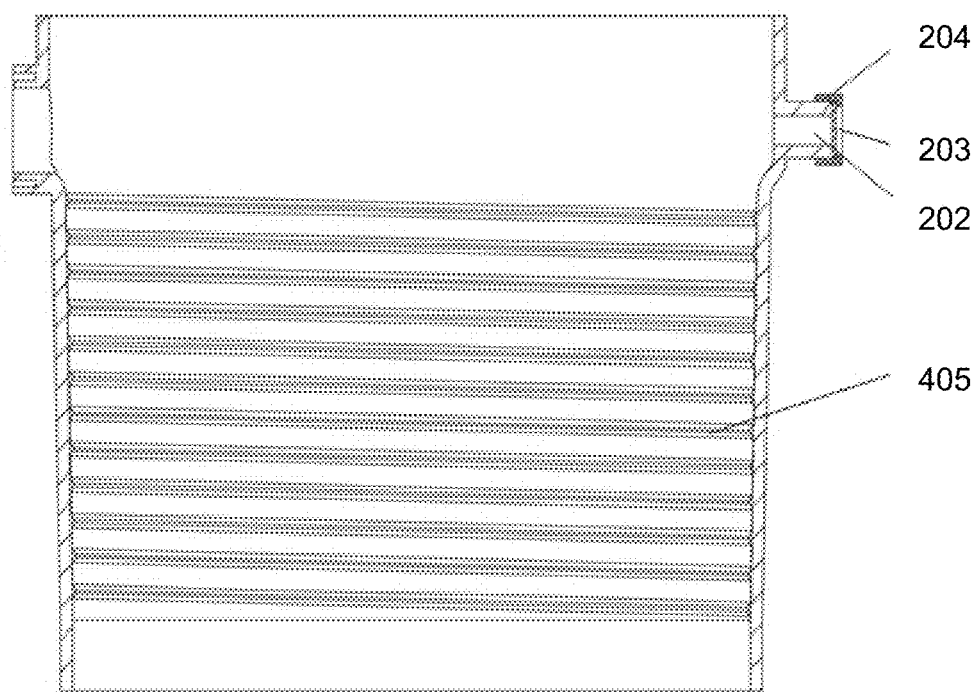
FIG. 2 is a schematic diagram illustrating a structure of a shell provided with a second vent according to some embodiments of the present disclosure.

FIG. 2 is a schematic diagram illustrating a structure of a shell provided with a second vent according to some embodiments of the present disclosure. In some embodiments, as shown in FIG. 2, the shell 20 may be further provided with a second vent 202. Since the shell 20 is cylindrical, some air bubbles may not reach near the mandrel 401, instead accumulate in an upper part of the shell 20, and the air bubbles may be discharged through the second vent 202. In some embodiments, the second vent 202 may be connected with other components using a hose for air discharging.

In some embodiments, the air bubbles accumulated in the upper part of the shell may be discharged by providing the second vent 202, and an air-discharging function may be better achieved in combination with the first vent 106, thereby improving the air bubble removal capacity of the membrane oxygenator.

In some embodiments, the second vent 202 may be provided with a one-way permeable membrane 203. For example, a compression cover 204 may be sleeved on the one-way permeable membrane 203. The compression cover 204 may be connected with the second vent 202 through threads or snaps to compress and fix the one-way permeable membrane 203. In some embodiments, the one-way permeable membrane 203 may have micropores that allow only air to pass through but not blood. Therefore, the second vent 202 provided with the one-way permeable membrane 203 may retain the blood and discharge the air bubbles from the blood without being connected with other components.

In some embodiments, the oxygenation structure 40 may be provided inside an inner cavity of the shell 20. The oxygenation structure 40 may include the mandrel 401, an oxygen pressure membrane 402, and the temperature-changing membrane 403. In some embodiments, the mandrel 401 may be provided in the first shell partition part, the oxygen pressure membrane 402 may be located between the first and the second shell partition parts, and the temperature-changing membrane 403 may be located between the inner wall of the shell 20 and the second shell partition part.

The mandrel 401 may be configured to converge and guide the oxygenated blood (i.e., the arterial blood) into the second blood path space 301. In some embodiments, the upper end of the mandrel 401 may enter the first blood pathway space 101, and a lower end of the mandrel 401 may be opposite to the blood outlet 305.

A structure of the mandrel 401 may include, but is not limited to, a cylindrical structure, a conical structure, etc. In some embodiments, the mandrel 401 may be set as a conical structure, so that a cross-section of the mandrel 401 may decrease gradually from the upper cover 10 to the lower cover 30, thereby better converging the oxygenated blood.

The oxygen pressure membrane 402 refers to a structure used for air exchange. In some embodiments, the oxygen pressure membrane 402 may connect the first gas path space 102 with the second gas path space 302.

In some embodiments, the oxygen pressure membrane 402 may include a plurality of ventilation pipes (not shown in the figure).

The ventilation pipes refer to tubes used for air exchange with the blood. In some embodiments, the ventilation pipes may be hollow pipes with openings at both ends, and aperture sizes of the ventilation pipes may be in a range of 0.1 μm to 5 μm. In some embodiments, one end of each ventilation pipe may be penetrated into a first plugging layer 501 and connected with the first gas path space 102, and the other end of each ventilation pipe may be penetrated into a second plugging layer 502 and connected with the second gas path space 302. In some embodiments, at least some of the plurality of ventilation pipes may have micropores on tube walls that allow only air to pass through and block red blood cells. In essence, the tube walls of the ventilation pipes may be considered as semi-permeable membranes that allow on air to pass through. The membrane oxygenator may realize a process of air exchange of blood through the semi-permeable membranes.

More details regarding the first plugging layer 501 and the second plugging layer 502 may be found in relevant descriptions below.

The temperature-changing membrane 403 may be used for heat exchange with blood to control blood temperature. In some embodiments, the temperature-changing membrane 403 may wrap an outer surface of the oxygen pressure membrane 402 and connect the first water path space 103 with the second water pathway space 303. In some embodiments, a gap 404 may be provided between the temperature-changing membrane 403 and the shell 20, and a width of the gap 404 may gradually decrease from the upper cover 10 to the lower cover 30. More details regarding the gap 404 may be found in FIG. 3 and relevant descriptions thereof.

In some embodiments, the temperature-changing membrane 403 may include a plurality of variable temperature tubes (not shown in the figure).

The variable temperature tubes refer to tubes used for heat exchange with the blood. In some embodiments, the variable temperature tubes may be hollow pipes with openings at both ends. One end of each variable temperature tube may be penetrated the first plugging layer 501 and connected with the first water path space 103, and the other end of each variable temperature tube may be penetrated into the second plugging layer 502 and connected with the second water path space 303.

In some embodiments, both the oxygen pressure membrane 402 and the temperature-changing membrane 403 may be composed of a large number of thin-wall hollow pipes. The difference is that the hollow pipes of the oxygen pressure membrane 402 may be at least partially porous tubes to enable air exchange with blood, while the hollow pipes of the temperature-changing membrane 403 may all be non-porous tubes to allow for diversion and heat exchange with blood outside the hollow pipes.

In some embodiments, after an assembly of the upper cover 10, the shell 20, the lower cover 30, and the oxygenation structure 40 is completed, the first blood path space 101 in the upper cover 10 may not be connected with the first gas path space 102, and the first gas path space 102 may not be connected with the first water path space 103 either. The second blood path space 301 in the lower cover 30 may not be connected with the second gas path space 302, and the second gas path space 302 may not be connected with the second water path space 303. In some embodiments, as shown in FIG. 1, the membrane oxygenator may also include the first plugging layer 501 and the second plugging layer 502. The first plugging layer 501 may be provided at a junction between the shell 20 and the upper cover 10, and the second plugging layer 502 may be provided at a junction between the shell 20 and the lower cover 30.

The first plugging layer 501 may be used to separate the inner cavity of the shell 20 from the spaces of the upper cover 10. In some embodiments, the first plugging layer 501 may be used to separate the first blood path space 101 and the first gas path space 102 from the first water path space 103, and separate the inner cavity of the shell 20 from the spaces of the upper cover 10.

The second plugging layer 502 may be used to separate the inner cavity of the shell 20 from the spaces of the lower cover 30. In some embodiments, the second plugging layer 502 may be used to separate the second blood path space 301 and the second gas path space 302 from the second water path space 303, and separate the inner cavity of the shell 20 from the spaces of the lower cover 30.

Figure 3:
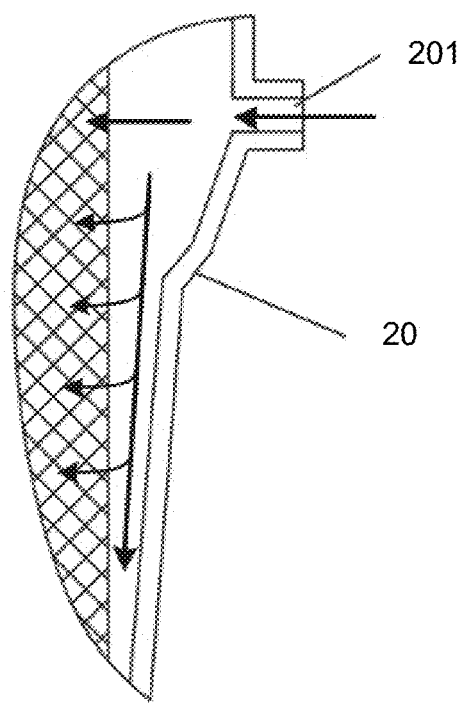
FIG. 3 is a partial schematic view illustrating a structure of a shell according to some embodiments of the present disclosure.

FIG. 3 is a partial schematic view illustrating a structure of a shell according to some embodiments of the present disclosure.

In some embodiments, as shown in FIG. 3, the shell 20 may be a cylindrical shell, and an inner diameter of the shell 20 may gradually decrease from the upper cover 10 to the lower cover 30. A cross-section of the mandrel 401 may also gradually decrease from the upper cover 10 to the lower cover 30.

In some embodiments, the gap 404 may be provided between the temperature-changing membrane 403 and the inner wall of the shell 20. The width of the gap 404 may gradually decrease from the upper cover 10 to the lower cover 30, the blood inlet 201 being close to the upper cover 10. Therefore, when blood enters the membrane oxygenator 100 through the blood inlet 201, the blood first fills the gap 404 between the temperature-changing membrane 403 and the inner wall of the shell 20. As the gap 404 gradually decreases from top to bottom, a small amount of blood fully fills a lower part of the gap 404, while more blood remains in an upper part of the gap 404. As a result, under driving by a continuous inflow of blood from the blood inlet 201, the blood remaining in the upper part of the gap 404 may continuously and laterally flow through the temperature-changing membrane 403 and the oxygen pressure membrane 402, then enter a space where the mandrel 401 is located, and finally return to the body through the blood outlet 305 connected with the space where the mandrel 401 is located.

In some embodiments, the gap 404 between the temperature-changing membrane 403 and the inner wall of the shell 20 gradually decreasing may be achieved by any one or a combination of the following manners.

(1) The shell 20 may be set as a cylindrical shape, so that the inner diameter of the shell 20 may gradually decrease from the upper cover 10 to the lower cover 30.

(2) The variable temperature tubes may be arranged, so that an end of the temperature-changing membrane 403 near the lower cover 30 may be closer to the inner wall of the shell 20 than an end of the temperature-changing membrane 403 near the upper cover 10.

In some embodiments, the gap 404 between the temperature-changing membrane 403 and the shell 20 gradually decreasing may also be achieved through other feasible manners.

In some embodiments of the present disclosure, as the gap between the temperature-changing membrane and the shell gradually decreases, the blood in the upper part of the gap may continuously and laterally flow through the temperature-changing membrane and the oxygen pressure membrane, thereby better ensuring the oxygenation effect of the membrane oxygenator.

Figure 4:
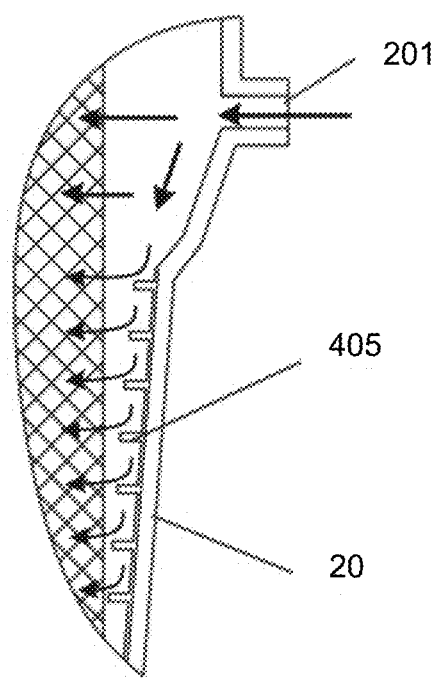
FIG. 4 is a partial schematic view illustrating another structure of a shell according to some embodiments of the present disclosure.

FIG. 4 is a partial schematic view illustrating another structure of a shell according to some embodiments of the present disclosure.

In some embodiments, as shown in FIG. 4, a spoiler structure may include a plurality of protrusions 405 protruding from the inner wall of the shell 20 towards the temperature-changing membrane 403. In some embodiments, blood may enter the gap between the inner wall of the shell 20 and the temperature-changing membrane 403 through the blood inlet 201. As the blood flows towards the lower cover 30, the blood may be obstructed by the protrusions 405, forcing the blood to change a flow direction and flow laterally into the temperature-changing membrane 403.

In some embodiments, the plurality of protrusions 405 of the spoiler structure may be distributed in a stepped manner, a distance between the protrusions 405 near the upper cover 10 and the temperature-changing membrane 403 being greater than a distance between the protrusions 405 near the lower cover 30 and the temperature-changing membrane 403. This arrangement may make the blood flowing towards the lower cover 30 be obstructed by the protrusions 405, thereby as much blood as possible laterally passing through the temperature-changing membrane 403 and the oxygen pressure membrane 402. An air exchange capacity is not only related to a surface area of the oxygen pressure membrane 402 and a concentration of oxygen from an air source, but also directly related to a setting of a blood flow route. Specifically, the higher the proportion of the blood flow route laterally passing through the oxygen pressure membrane, the better the effect of the oxygenator.

In some embodiments, the plurality of protrusions 405 of the spoiler structure may be arranged in a spiral step pattern on the inner wall of the shell 20, thereby guiding the blood to flow in a spiral pattern through spirally extended grooves on the inner wall of the shell 20.

In some embodiments, the protrusions 405 may be dotted, and a plurality of dotted protrusions 405 may form a spiral step pattern. In some embodiments, the protrusions 405 may be integral and have the spiral step pattern. In some embodiments, there may be one or a plurality of spiral stepped protrusions 405.

In some embodiments, a starting point of the spiral step grooves may be provided below the blood inlet 201. In some embodiments, as the spiral step pattern extends downward, a degree of protrusion of the protrusions 405 that form the spiral step pattern may gradually decrease.

The blood spirally rotates and flows by setting the spiral spoiler structure, reducing damage to the blood caused by a flow resistance, and increasing air exchange between the blood and the oxygen pressure membrane.

In some embodiments, the lateral flow of blood through the temperature-changing membrane and the oxygen pressure membrane may be facilitated through the spoiler structure, thereby achieving sufficient heat exchange and air exchange, which is conductive to improving the oxygenation effect of the membrane oxygenator.

A way of use and a working process of the membrane oxygenator provided in some embodiments of the present disclosure are as follows.

During a surgery or maintenance of vital signs, the blood inlet 201 is connected with a vein of a human body via a hose, the blood outlet 305 is connected with an artery of the human body via a hose, the water inlet 104 and the water outlet 306 are respectively connected with a variable temperature water tank via hoses, and the air inlet 105 is connected with an air source via a hose. The water at a set temperature may be introduced into the inner cavities of the variable temperature tubes of the temperature-changing membrane 403 from the variable temperature water tank through the water inlet 104, and oxygen at a preset concentration may be introduced into inner cavities of ventilation pipes of the oxygen pressure membrane 402 from the air source through the air inlet 105. In this way, when venous blood enters the shell 20 through the blood inlet 201, the blood passing through the temperature-changing membrane 403 undergoes heat exchange with outer walls of the variable temperature tubes, achieving the purpose of warming or cooling the blood. Afterwards, the venous blood completing the heat exchange flows laterally into the oxygen pressure membrane 402. Gas is inside the ventilation pipes, and blood is outside the ventilation pipes, and the gas and the blood on both sides of the semi-permeable membranes exchange oxygen and carbon dioxide by diffusion across the semi-permeable membranes. In this case, the carbon dioxide in the venous blood enters the inner cavities of the ventilation pipes, while the oxygen in the ventilation pipes enter the blood, thereby completing a process of transforming the venous blood into the arterial blood. The arterial blood then returns to the human body through the blood outlet 305, maintaining oxygen supply to the patient. The membrane oxygenator functions in a way similar to or consistent with the lung functions of the human body.

In some embodiments, the blood inlet may be disposed at the upper part of the shell, and the blood outlet may be disposed at the lower cover. When blood enters the membrane oxygenator, the blood first fills a space between the temperature-changing membrane and the shell. As a structure of the space gradually decreases, the injected blood may quickly fill a lower part of the space, allowing subsequently injected blood to stay longer in an upper part of the space, thereby making more blood laterally enter the temperature-changing membrane. In this way, under driving by a continuous inflow of the blood into the oxygenator, the blood entering the temperature-changing membrane may continuously and laterally flow into the oxygen pressure membrane, then reach the mandrel, and flow out of a lower part of the mandrel through the blood outlet. Furthermore, a proportion of the blood flowing laterally through the oxygen pressure membrane is increased, improving the oxygenation effect of the membrane oxygenator, and achieving a relatively high air exchange capacity with a relatively small oxygen pressure membrane area. In addition, with more blood flowing laterally through the oxygenator, a resistance loss of the oxygenator may be reduced, thereby reducing damage to the blood caused by the resistance.

Figure 5:
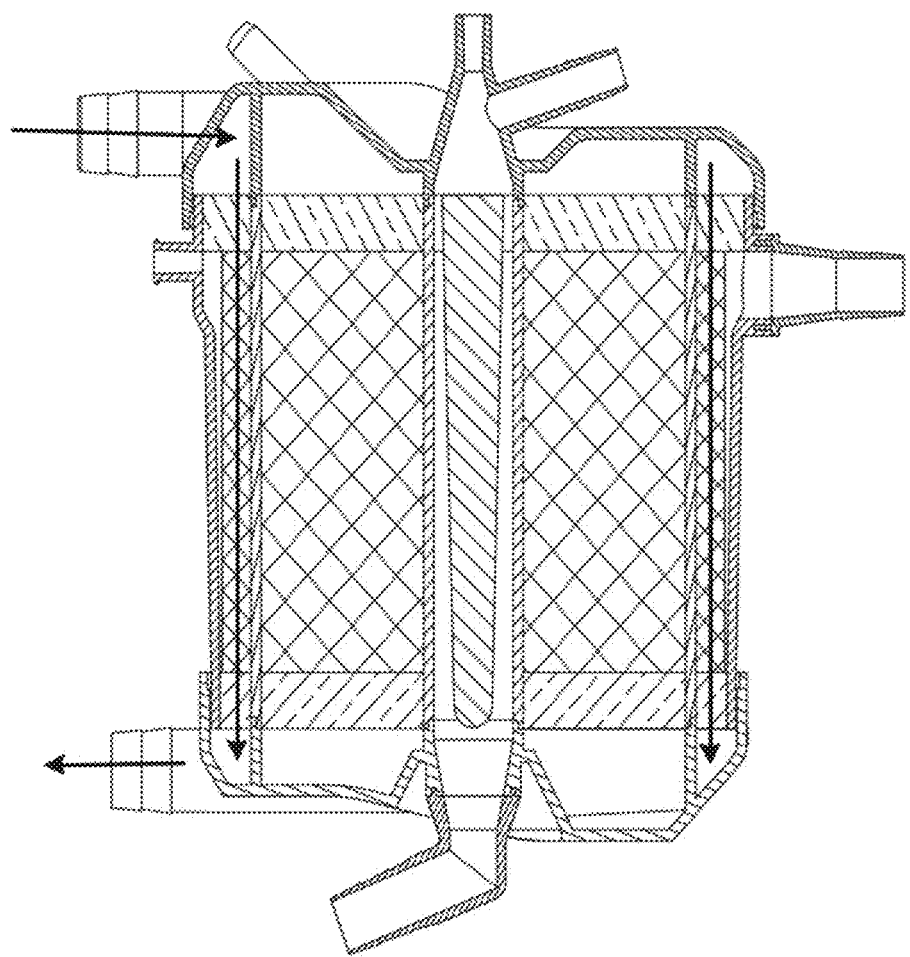
FIG. 5 is a schematic diagram illustrating a flow direction of water in a membrane oxygenator according to some embodiments of the present disclosure.

FIG. 5 is a schematic diagram illustrating a flow direction of water in a membrane oxygenator according to some embodiments of the present disclosure.

As shown in FIG. 5, in some embodiments, water from a variable temperature water tank may enter the first water path space 103 through the water inlet 104, pass through variable temperature tubes, and enter the second water path space 303. Then, the water may return to the variable temperature water tank through the water outlet 306. During this process, blood flowing through the variable temperature tubes may undergo heat exchange with the water inside the variable temperature tubes, and a temperature of the blood may be adjusted to a desired temperature.

Figure 6:
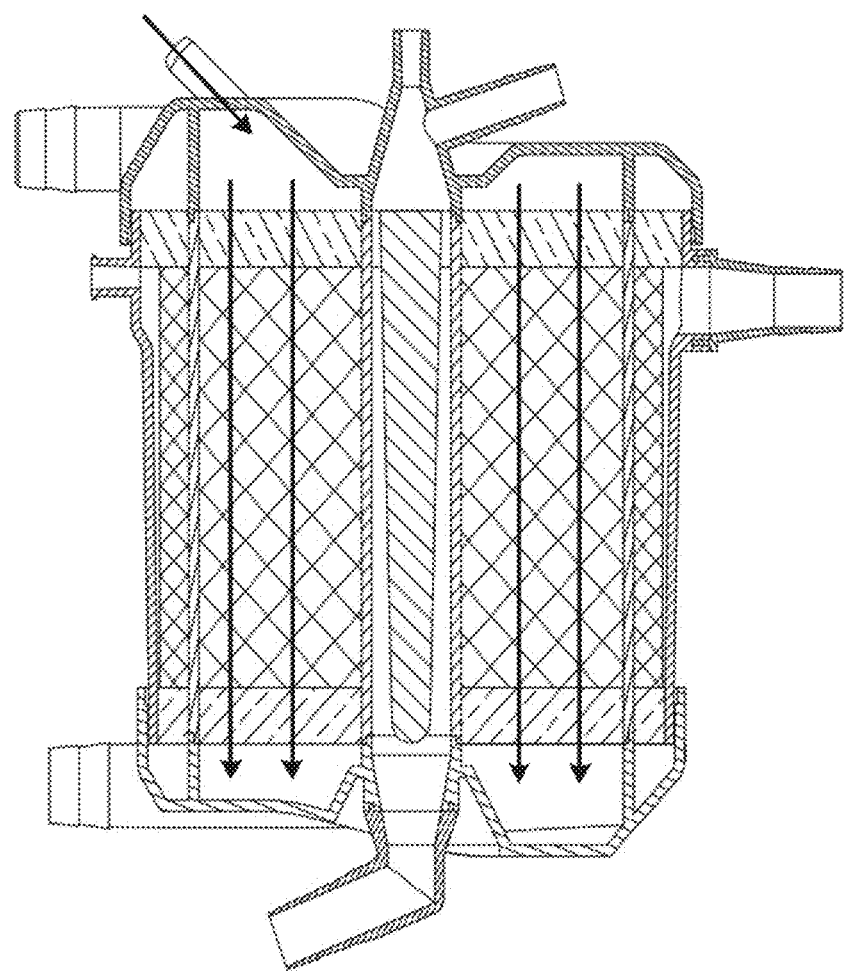
FIG. 6 is a schematic diagram illustrating a flow direction of air in a membrane oxygenator according to some embodiments of the present disclosure.

FIG. 6 is a schematic diagram illustrating a flow direction of air in a membrane oxygenator according to some embodiments of the present disclosure.

As shown in FIG. 6, in some embodiments, oxygen from an air source may enter the first gas path space 102 through the air inlet 105, then flows into ventilation pipes, and blood passing through the ventilation pipes may undergo air exchange with the ventilation pipes. Specifically, the oxygen in the ventilation pipes may combine with the blood, carbon dioxide in the blood may enter the ventilation pipes, and then the carbon dioxide in the blood may flow into the second gas path space 302 and discharge from the air outlet.

Figure 7:
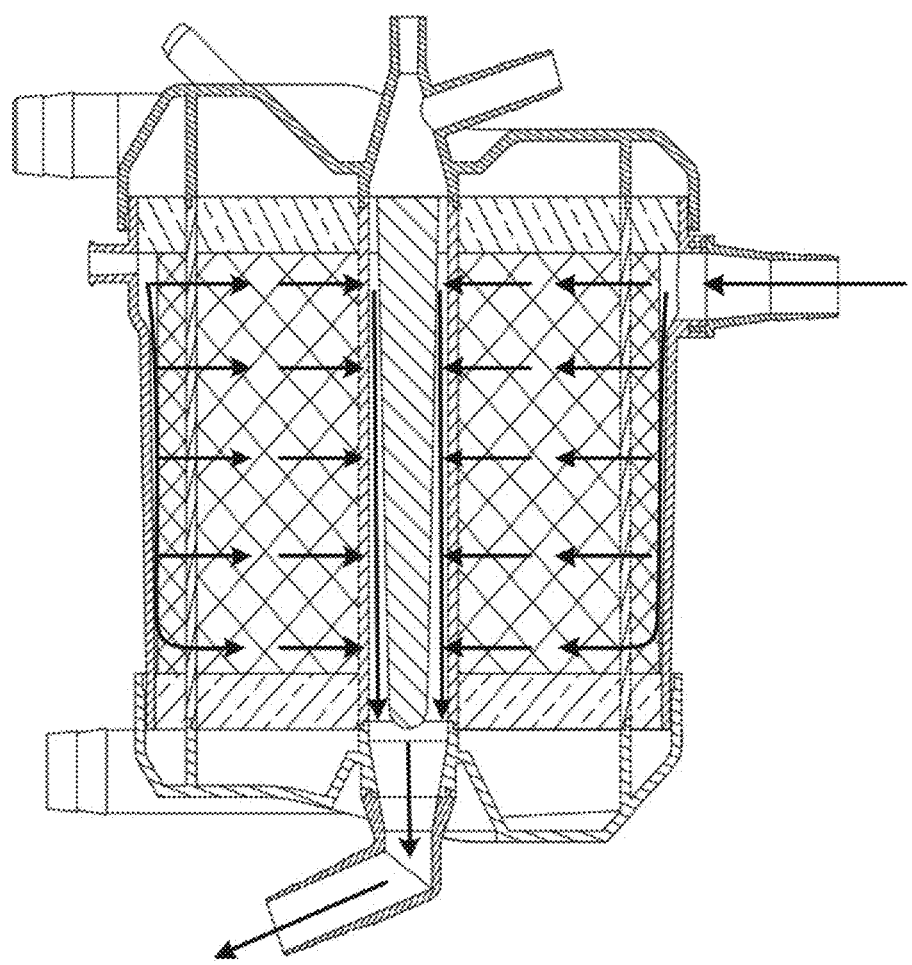
FIG. 7 is a schematic diagram illustrating a flow direction of blood in a membrane oxygenator according to some embodiments of the present disclosure.

FIG. 7 is a schematic diagram illustrating a flow direction of blood in a membrane oxygenator according to some embodiments of the present disclosure.

As shown in FIG. 7, in some embodiments, blood may enter the membrane oxygenator through the blood inlet 201 and laterally pass through the temperature-changing membrane 403 and the oxygen pressure membrane 402 before converging in a space where the mandrel 401 is located, and then flow out through the blood outlet 305.

In some embodiments, due to a relatively large blood flow buffer region of the membrane oxygenator, when the blood enters the oxygenator, more blood may pass through the temperature-changing membrane and the oxygen pressure membrane at a relatively slow rate. The blood may be in contact with the temperature-changing membrane and the oxygen pressure membrane for a longer period of time, which results in better variable temperature efficiency and oxygenation effect. This design also reduces a resistance loss of the oxygenator, thereby reducing damage to the blood caused by the resistance.

In some embodiments, the membrane oxygenator may have an air bubble removal capacity. Specifically, by arranging the air outlets reasonably, the air bubbles in the membrane oxygenator may be easily discharged, avoiding bubble accumulation, and eliminating complicated discharging operations. As the air bubbles in the blood move upward, the air bubbles may be easily discharged through a first vent on a top of an upper cover by allowing air inside the oxygenator to accumulate near the mandrel along a blood flow. A user may effortlessly remove the air bubbles without tapping or rotating the oxygenator, visually observe residual air bubbles inside the oxygenator through the transparent upper cover, and determine a safety risk in the product (the membrane oxygenator) or an overall circuit by observing the air bubbles accumulating at the top of the upper cover during a surgery, thereby facilitating taking measures in time to avoid severe consequences.

In some embodiments, the membrane oxygenator may include a processor. The processor may be configured to process data related to a function of the membrane oxygenator.

In some embodiments, the processor may control a temperature of inflowing water at the water inlet 104 based on a warming rate or a cooling rate for clinical need. For example, the processor may be communicatively connected with the variable temperature water tank to control the variable temperature water tank to warm or cool water in the variable temperature water tank at a preset warming rate or cooling rate by controlling power of the variable temperature water tank, thereby ensuring that the inflow water at the water inlet 104 reaches a target temperature within a set time in time, realizing a temperature change of the inflow water in time, and satisfying the clinical need.

In some embodiments, the processor may further control a volume and a flow rate of inflow air based on an oxygenation rate and a carbon dioxide removal rate for clinical need.

The oxygenation rate refers to a rate at which blood is oxygenated, while the carbon dioxide removal rate refers to a rate at which carbon dioxide is removed from blood. In some embodiments, the oxygenation rate and the carbon dioxide removal rate may be obtained by measuring contents of oxygen and carbon dioxide in blood with a blood gas analyzer. For example, the contents of oxygen and carbon dioxide in the blood may be measured before and after the blood passes through the membrane oxygenator at a set interval, and then the oxygenation rate and the carbon dioxide removal rate may be calculated accordingly.

In some embodiments, the volume and the flow rate of the inflow air may be adjusted accordingly if there is a difference between the oxygenation rate for the clinical need and an actually measured oxygenation rate and a difference between the carbon dioxide removal rate for the clinical need and an actually measured carbon dioxide removal rate. For example, if the oxygenation rate for the clinical need is greater than the actual measured oxygenation rate, and the difference between the oxygenation rate for the clinical need and the actual measured oxygenation rate exceeds a preset threshold, then at least one of the volume or the flow rate of the inflow air may be increased.

In some embodiments, the flow rate of the inflow air may be positively correlated with an amount of removed carbon dioxide. For example, when a proportion of carbon dioxide within a unit time or a content of carbon dioxide within the unit time at an air outlet is relatively high, the flow rate of the inflow air may be increased. The proportion of carbon dioxide within the unit time is defined as a result of dividing the content of carbon dioxide within the unit time by a total air content within the unit time at the air outlet.

In some embodiments, the membrane oxygenator may also include a notification module and at least one sensor. The notification module and the at least one sensor may be communicatively connected with the processor. The at least one sensor may include a flow sensor, a temperature sensor, and a chemical sensor (e.g., a carbon dioxide sensor, an oxygen sensor, etc.). In some embodiments, the at least one sensor may be at least deployed at the blood inlet 201 and the blood outlet 305 of the membrane oxygenator for collecting data related to the blood flowing through the membrane oxygenator. The notification module may be configured to display or issue a warning message. In some embodiments, the notification module may have a display screen for showing the warning message. In some embodiments, the notification module may emit a beep or a human voice alert. In some embodiments, the notification module may display the warning message on the display screen while simultaneously issuing the human voice alert.

In some embodiments, the processor may be further configured to: collect multi-dimensional sensor data from the at least one sensor; evaluate a probability of abnormal performance of the membrane oxygenator based on the multi-dimensional sensor data; and control the notification module to display or issue the warning message in response to the probability of abnormal performance of the membrane oxygenator satisfying a preset condition. The multi-dimensional sensor data may include at least one of flow data, temperature data, and chemical data of one or more preset points. In some embodiments, the preset points may be set according to the clinical need. For example, the preset points may be located at the blood inlet 201 or the blood outlet 305 of the membrane oxygenator. In some embodiments, at least one sensor may be disposed at each preset point. More details regarding the preset points may be found in the descriptions below.

In some embodiments, based on the multi-dimensional sensor data collected from the at least one sensor, if a blood indicator of the blood outlet does not satisfy a preset condition, it is considered that the membrane oxygenator may have abnormal performance. The blood indicator of the blood outlet not satisfying the preset condition may include: the content of oxygen in the blood not reaching an oxygen standard value or the content of carbon dioxide in the blood exceeding a carbon dioxide standard value. The oxygen standard value and the carbon dioxide standard value may be set manually based on experience. In some embodiments, the processor may evaluate a probability value of abnormal performance of the membrane oxygenator based on a numerical value of the content of oxygen in the blood not reaching the oxygen standard value or a numerical value of the content of carbon dioxide in the blood exceeding the carbon dioxide standard value. A difference between the numerical value of the content of oxygen in the blood not reaching the oxygen standard value and the numerical value of the content of carbon dioxide in the blood exceeding the carbon dioxide standard value may be positively correlated with the probability value of the abnormal performance, i.e., the larger the difference, the higher the probability value of the abnormal performance.

In some embodiments, the notification module may issue the warning message based on the abnormal performance of the membrane oxygenator or the probability value of the abnormal performance of the membrane oxygenator exceeding a preset probability threshold. In some embodiments, the user may adjust operating parameters of the membrane oxygenator based on the warning message, for example, by increasing or decreasing the volume of the inflow air, etc.

In some embodiments, the membrane oxygenator may collect sensor data in real time through the at least one sensor and perform self-assessment of a performance status of the sensor data based on the sensor data, thereby early discovering a potential anomaly and issuing the warning message in time, and improving the use safety of the device.

In some embodiments, the at least one sensor may be deployed at the one or more preset points in a blood circulation loop inside the membrane oxygenator.

In some embodiments, the processor may further evaluate a probability of abnormal performance of each preset region inside the membrane oxygenator based on the multi-dimensional sensor data collected from the at least one sensor, and evaluate the probability of abnormal performance of the membrane oxygenator based on the probability of abnormal performance of each preset region.

In some embodiments, the processor may independently evaluate the performance probability based on sensor data collected by each sensor. For example, the processor may evaluate a probability of abnormal performance of a region corresponding to a location of a sensor inside the membrane oxygenator based on a difference between standard data of the location of the sensor and data measured by the sensor. The standard data of the location of the sensor may be preset or obtained through an experiment. If the difference between the standard data of the location of the sensor and the data measured by the sensor exceeds a preset data threshold, it is considered that the region corresponding to the location of the sensor may have the abnormal performance. In some embodiments, the difference between the standard data of the location of the sensor and the data measured by the sensor may be positively correlated with the probability value of the abnormal performance. Specifically, the larger the difference, the higher the probability value of the abnormal performance.

In some embodiments, the processor may evaluate the probability of abnormal performance of each preset region inside the membrane oxygenator by constructing a model.

In some embodiments, the processor may construct a blood flow feature map based on a blood flow situation inside the membrane oxygenator. The blood flow feature map may include nodes and edges. The nodes may include the preset points where the sensors are located, and the edges may include flow relationships between the nodes. Node features may include multi-dimensional sensor data at a plurality of time points, and edges features may include a distance and a flow feature. The flow feature may include a blood flow rate, which may be measured. For example, the blood flow rate may be measured with a Doppler ultrasound diagnostic device.

In some embodiments, the processor may determine, based on the blood flow feature map, an abnormal probability of each node through a prediction model. The prediction model may be a machine learning model. The prediction model may include any one or a combination of a Graph Neural Network (GNN) model or other customized model structures. In some embodiments, an input of the prediction model may include the blood flow feature map, and an output of the prediction model may include the abnormal probability of each node. As each node includes each preset point where the at least one sensor is located, the abnormal probability of each node may be the probability of abnormal performance of each preset region.

In some embodiments, the prediction model may be trained based on a large number of first labeled training samples. The first training samples may be sample fluid flow features maps, and labels may be an abnormal probability of each node corresponding to each sample blood flow characteristic map. The first training samples and the labels may be obtained from historical data. The labels may be manually annotated.

In some embodiments, the probability of abnormal performance of each preset region inside the membrane oxygenator may be efficiently and accurately evaluated by constructing the blood flow feature map, inputting the blood flow feature map into the prediction model, and outputting the probability of abnormal performance of each preset region through the prediction model.

In some embodiments, the processor may obtain, based on the probability of abnormal performance of each preset region inside the membrane oxygenator, an overall probability of abnormal performance of the membrane oxygenator (as a whole) in various feasible ways. For example, the processor may obtain the overall probability of abnormal performance of the membrane oxygenator (as a whole) through summation, weighted summation, etc.

In some embodiments, a length of blood flow between any two preset points of the one or more preset points of the membrane oxygenator may be at least not smaller than a first distance.

The first distance may be determined based on the blood flow rate, which may be estimated. In some embodiments, the processor may determine the first distance based on an estimated blood flow rate, and a difference of blood temperature or a parameter difference before and after air exchange. For example, the greater the blood flow rate, and the smaller the difference of blood temperature or the parameter difference before and after air exchange (e.g., a small difference in blood temperature, or a small difference in the content of oxygen), the greater the first distance. In some embodiments, the greater the blood flow rate, and the smaller the difference of blood temperature or the parameter difference before and after air exchange, it is considered that features of blood at two adjacent points inside the membrane oxygenator may not change essentially. Therefore, a relatively larger first distance may be set, ensuring that the sensors are not disposed too close, preventing the function of the membrane oxygenator from being interfered by the densely disposed sensors, and avoiding wastage of resources.

In some embodiments, before the membrane oxygenator is put into use, the one or more preset points may be determined based on a predetermined first distance. For example, locations of the at least one sensor may be deployed in a matrix array, so that a distance between any two preset points may be greater than or equal to the first distance.

The basic concept has been described above. Obviously, for those skilled in the art, the above detailed disclosure is only an example, and does not constitute a limitation to the present disclosure. Although not expressly stated here, those skilled in the art may make various modifications, improvements and corrections to the present disclosure. Such modifications, improvements and corrections are suggested in this disclosure, so such modifications, improvements and corrections still belong to the spirit and scope of the exemplary embodiments of the present disclosure.

Meanwhile, the present disclosure uses specific words to describe the embodiments of the present disclosure. For example, "one embodiment", "an embodiment", and/or "some embodiments" refer to a certain feature, structure or characteristic related to at least one embodiment of the present disclosure. Therefore, it should be emphasized and noted that references to "one embodiment" or "an embodiment" or "an alternative embodiment" two or more times in different places in the present disclosure do not necessarily refer to the same embodiment. In addition, certain features, structures or characteristics in one or more embodiments of the present disclosure may be properly combined.

In some embodiments, counts describing the quantity of components and attributes are used. It should be understood that such counts used in the description of the embodiments use the modifiers "about", "approximately" or "substantially" in some examples. Unless otherwise stated, "about", "approximately" or "substantially" indicates that the stated figure allows for a variation of ±20%. Accordingly, in some embodiments, the numerical parameters used in the disclosure and claims are approximations that can vary depending upon the desired characteristics of individual embodiments. In some embodiments, numerical parameters should consider the specified significant digits and adopt the general digit retention method. Although the numerical ranges and parameters used in some embodiments of the present disclosure to confirm the breadth of the range are approximations, in specific embodiments, such numerical values are set as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it should be understood that the embodiments described in the present disclosure are intended to illustrate the principles of the embodiments disclosed herein. Other variations may also fall within the scope of the present disclosure. Therefore, by way of example and not limitation, alternative configurations of the embodiments disclosed in the present disclosure may be considered consistent with the teachings of the present disclosure. Accordingly, the embodiments described in the present disclosure are not limited to the explicitly introduced and described embodiments in the present disclosure.

What is claimed is:
1. A membrane oxygenator, comprising:
an upper cover sequentially divided into a first blood path space, a first gas path space, and a first water path space from a center to an outer edge, and the upper cover being provided with an air inlet connected with the first gas path space, a first vent connected with the first blood path space, and a water inlet connected with the first water path space;

a lower cover sequentially divided into a second blood path space, a second gas path space, and a second water path space from a center to an outer edge, and the lower cover being provided with a blood outlet connected with the second blood path space, an air outlet connected with the second gas path space, and a water outlet connected with the second water path space;

a shell, both ends of the shell being connected with the upper cover and the lower cover respectively, a blood inlet connected with an inner cavity of the shell being provided on the shell near the upper cover;

an oxygenation structure provided in the inner cavity of the shell, including a mandrel, an oxygen pressure membrane, and a temperature-changing membrane, an upper end of the mandrel entering the first blood path space, the upper end of the mandrel being opposite to the first vent, a lower end of the mandrel being opposite to the blood outlet, the oxygen pressure membrane being provided around the mandrel, the oxygen pressure membrane connecting the first gas path space and the second gas path space, the temperature-changing membrane wrapping around the oxygen pressure membrane, and the temperature-changing membrane being connected with the first water path space and the second water path space; a gap being provided between the temperature-changing membrane and an inner wall of the shell, a width of the gap gradually decreasing from the upper cover to the lower cover; and a spoiler structure for directing a lateral flow of blood, the spoiler structure being provided between the shell and the temperature-changing membrane, the spoiler structure including a plurality of protrusions protruding from the inner wall of the shell towards the temperature-changing membrane, and the plurality of protrusions being provided on the inner wall of the shell.

2. The membrane oxygenator of claim 1, wherein the membrane oxygenator further includes:
a first plugging layer provided at a junction of the shell and the upper cover;
a second plugging layer provided at a junction of the shell and the lower cover.

3. The membrane oxygenator of claim 2, wherein the oxygen pressure membrane includes a plurality of ventilation pipes, the ventilation pipes being hollow pipes with openings at both ends; one end of each ventilation pipe being penetrated into the first plugging layer and connected with the first gas path space, and the other end of each ventilation pipe being penetrated into the second plugging layer and connected with the second gas path space.

4. The membrane oxygenator of claim 2, wherein the temperature-changing membrane includes a plurality of variable temperature tubes, the variable temperature tubes being hollow pipes with openings at both ends; one end of each variable temperature tube being penetrated into the first plugging layer and connected with the first water path space, and the other end of each variable temperature tube being penetrated into the second plugging layer and connected with the second water path space.

5. The membrane oxygenator of claim 1, wherein the plurality of protrusions are distributed in a stepped manner, and a distance between protrusions close to the upper cover and the temperature-changing membrane is greater than a distance between protrusions close to the lower cover and the temperature-changing membrane.

6. The membrane oxygenator of claim 1, wherein the upper cover is further provided with a recirculation port, the recirculation port being connected with the first vent.

7. The membrane oxygenator of claim 1, wherein the shell is provided with a second vent.

8. The membrane oxygenator of claim 7, wherein the second vent is provided with a one-way permeable membrane, the one-way permeable membrane being used to retain liquid in the shell and allow air bubbles in the liquid to discharge from the shell.

9. The membrane oxygenator of claim 1, wherein the shell is a cylindrical shell and an inner diameter of the shell decreases sequentially from the upper cover to the lower cover; and
a cross-section of the mandrel decreases gradually from the upper cover to the lower cover.

10. The membrane oxygenator of claim 1, wherein the upper cover includes a first partition ring and a second partition ring, the second partition ring being provided around the first partition ring, the first partition ring separating the first blood path space from the first gas path space, and the second partition ring separating the first gas path space from the first water path space;
the lower cover includes a third partition ring and a fourth partition ring, the fourth partition ring being provided around the third partition ring, the third partition ring separating the second blood path space from the second gas path space, and the fourth partition ring separating the second gas path space from the second water path space.

* * * * *